United States Patent
Ciciarelli et al.

[19]

[11] Patent Number: 5,968,083
[45] Date of Patent: Oct. 19, 1999

[54] ACTIVE OVERLOAD DETECTION AND PROTECTION CIRCUIT FOR IMPLANTABLE CARDIAC THERAPY DEVICES

[75] Inventors: Timothy E. Ciciarelli; Stephen T. Archer, both of Sunnyvale, Calif.

[73] Assignee: Pacesetter, Inc., Sunnyvale, Calif.

[21] Appl. No.: 08/968,242

[22] Filed: Nov. 12, 1997

[51] Int. Cl.[6] .................................................... A61N 1/08
[52] U.S. Cl. ................................. 607/62; 607/2; 361/58; 361/59
[58] Field of Search ................................. 607/2, 4–6, 9, 607/62, 63, 27; 128/901, 902, 908; 361/58, 59

[56] References Cited

U.S. PATENT DOCUMENTS

| | | | |
|---|---|---|---|
| 4,745,923 | 5/1988 | Winstrom | 607/9 |
| 5,720,767 | 2/1998 | Amely-Velez | 607/63 |
| 5,761,019 | 6/1998 | Kroll | 361/58 |

*Primary Examiner*—William E. Kamm
*Assistant Examiner*—Kennedy J. Schaetzle
*Attorney, Agent, or Firm*—Steven M. Mitchell

[57] ABSTRACT

An active overload detection and protection circuit for protecting a host device (e.g., an implantable cardiac therapy device) from potential damage due to high voltage transients applied to an I/O node thereof. The protection circuit includes an I/O circuit coupled to the I/O node, the I/O circuit having low-impedance and high-impedance modes, a current overload detection circuit coupled to the I/O circuit which detects a current overload condition induced by a high voltage transient, and which generates an overload detect signal in response, and, a mode changing circuit which changes the mode of the I/O circuit from the low-impedance mode to the high-impedance mode in response to the overload detect signal. The protection circuit further includes a reset circuit which generates a reset signal a prescribed time after the overload detect signal is generated, wherein the mode changing circuit is responsive to the reset signal to change the mode of the I/O circuit. The current overload detection circuit includes circuitry which ensures that the overload detect signal is generated only when an overload current flowing through the I/O circuit is greater than a prescribed threshold level for at least a prescribed time period. The mode changing circuit includes logic circuitry which generates a mode change control signal only when both the overload detect signal and a first control signal are present.

18 Claims, 1 Drawing Sheet

5,968,083

ACTIVE OVERLOAD DETECTION AND PROTECTION CIRCUIT FOR IMPLANTABLE CARDIAC THERAPY DEVICES

BACKGROUND OF THE INVENTION

The present invention relates generally to implantable cardiac therapy devices, and more particularly, to an active overload detection and protection circuit for such devices.

Implantable cardiac therapy devices include implantable pacemakers and implantable cardioverter-defibrillators. An implantable pacemaker monitors the intrinsic electrical activity of the patient's heart and if a natural heart beat is not detected within a prescribed time period, the pacemaker delivers (via a lead system) an electrical stimulation or pacing pulse to force the heart muscle tissue to contract, thereby assuring that a minimum heart rate is maintained. In this way, bradycardia is terminated or prevented. Contemporary implantable cardioverter-defibriliators (ICDs) monitor the intrinsic electrical activity of the patient's heart in accordance with a diagnostic or detection algorithm by analyzing electrograms (EGMs) generated by sensing electrodes positioned proximate the sino-atrial and/or atrio-ventricular node of the patient's heart, and most advantageously, in the right ventricular apex of the patient's heart.

Typical current-generation ICDs are capable of delivering various types or levels of cardiac therapy (i.e., "tiered therapy"). The first type or level of therapy is bradycardia and antitachycardia pacing (ATP), in which a low level of electrical energy (generally between millionths to thousandths of a joule) is delivered to the patient's heart (via a lead system) in order to correct detected episodes of bradycardia or tachycardia, respectively. The second type or level of therapy is cardioversion, in which an intermediate level of electrical energy (generally between 1–5 joules) is delivered to the patient's heart (via a lead system) to terminate a detected episode of ventricular arrhythmia (e.g., a detected heart beat in the range of 130–190 beats/minute) or an ongoing episode of tachycardia that ATP therapy has failed to tenninate. The third type or level of therapy is defibrillation, in which a high level of electrical energy (generally above 15 joules) is delivered to the patient's heart (via a lead system) in order to terminate a detected episode of ventricular fibrillation or an episode of ventricular tachycardia which has degraded into ventricular fibrillation due to failure of cardioversion therapy. The defibrillation energy is typically stored in a defibrillation energy storage capacitor ("output capacitor") which is charged by a high-voltage charging circuit, and then delivered as an electrical shock(s) by means of a high-voltage output switching circuit which discharges the output capacitor.

At various times during normal operation of an implantable cardiac therapy device, the device circuitry is particularly susceptible to being damaged by external high voltage transients, such as those produced when the patient is subjected to external defibrillation. Such external high voltage transients can induce large (>150 mA) and slow (longer than 10 ns) current pulses within the device circuitry, which can cause significant damage to the device circuitry. Presently available ICDs include passive protection circuitry to prevent such current overload conditions from arising and damaging the device. Since this protection circuitry is passive, it does not have the capability of actively detecting a current overload condition. Further, the passive current overload protection circuitry is inadequate to protect the device circuitry against certain current overload conditions, such as those occasioned by external high voltage transients encountered during external defibrillation, especially during periods when the device is particularly vulnerable to damage, e.g., during pacing, plethesmography, and output capacitor discharge periods.

Based on the above, it can be appreciated that there presently exists a need in the art for an implantable cardiac therapy device which overcomes the above-described disadvantages and shortcomings of the presently available devices. More particularly, there presently exists a need in the art for an implantable cardiac therapy device which includes an active overload detection and protection circuit which is capable of actively detecting a current overload condition and of placing the device in a current overload protection mode which minimizes potential damage to the device circuitry. The present invention fulfills this need in the art.

SUMMARY OF THE INVENTION

The present invention encompasses an active overload detection and protection circuit for protecting a host device (e.g., an implantable cardiac therapy device) from potential damage due to high voltage transients applied to an I/O node thereof. The protection circuit includes an I/O circuit coupled to the I/O node, the I/O circuit having low-impedance and high-impedance modes, a current overload detection circuit coupled to the I/O circuit which detects a current overload condition induced by a high voltage transient applied to the I/O node, and which generates an overload detect signal in response to detecting a current overload condition, and, a mode changing circuit which changes the mode of the I/O circuit from the low-impedance mode to the high-impedance mode in response to the overload detect signal.

In the disclosed embodiment, the protection circuit further includes a reset circuit which generates a reset signal a prescribed time after the overload detect signal is generated, wherein the mode changing circuit is responsive to the reset signal to change the mode of the I/O circuit from the high-impedance mode to the low-impedance mode.

In the disclosed embodiment, the current overload detection circuit includes circuitry which ensures that the overload detect signal is generated only when an overload current flowing through the I/O circuit is greater than a prescribed threshold level for at least a prescribed time period.

In the disclosed embodiment, the mode changing circuit includes logic circuitry which generates a mode change control signal only when both the overload detect signal and a first control signal are present, and mode changing circuitry which changes the mode of the I/O circuit from the low-impedance mode to the high-impedance mode in response to the mode change control signal. In one embodiment, the first control signal is present only when the host device is in a prescribed operating mode in which it is particularly vulnerable to damage due to the high voltage transients.

BRIEF DESCRIPTION OF THE DRAWINGS

These and various other features and advantages of the present invention will be more clearly understood from the following detailed description taken in conjunction with the accompanying drawing, in which.

DETAILED DESCRIPTION OF THE INVENTION

Figure 1:
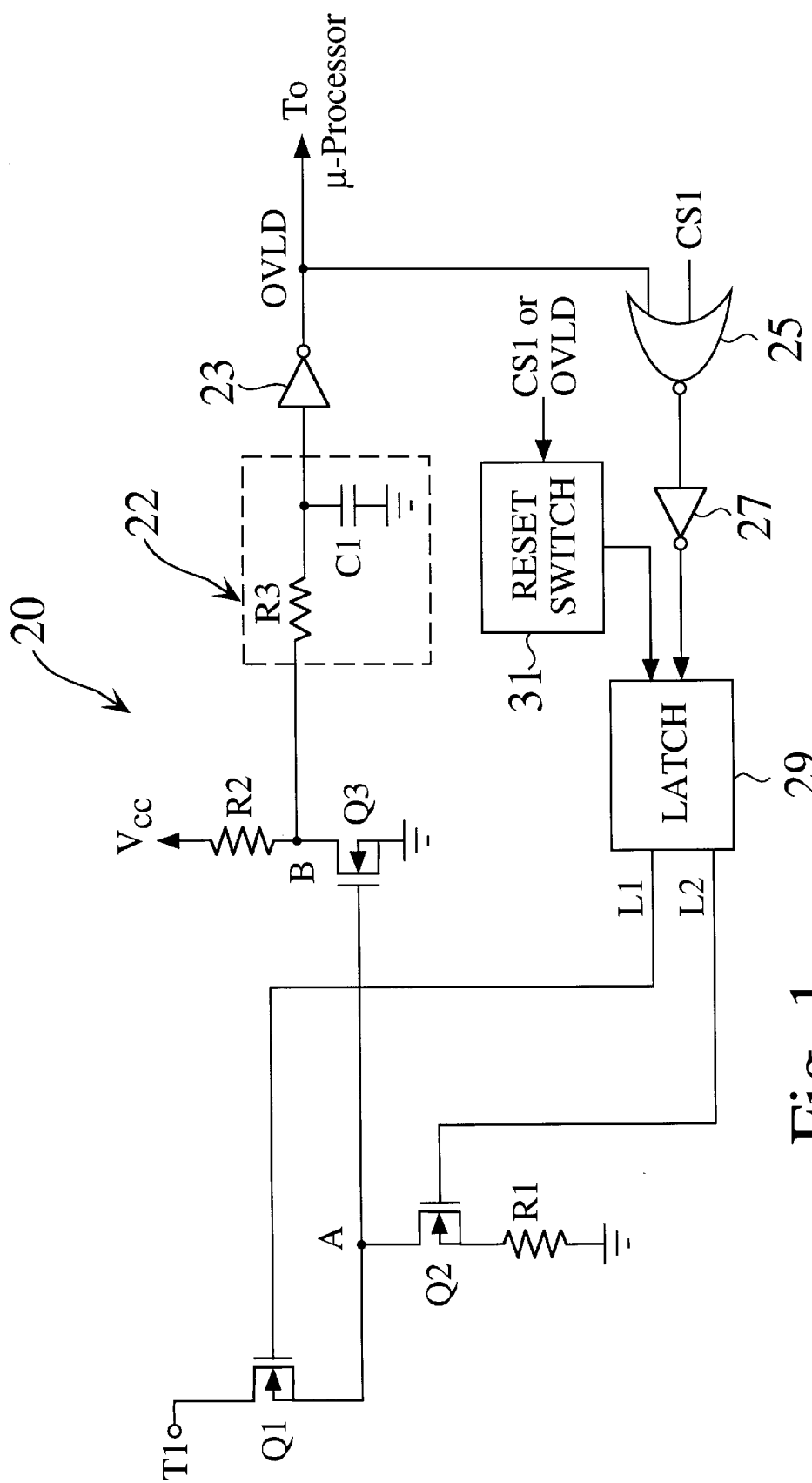
FIG. 1 is a schematic diagram of the active overload and protection circuit of a prototype implementation of the present invention.

With reference now to FIG. 1, there can be seen a schematic diagram of a current overload detection and protection circuit 20 which constitutes a prototype implementation of the present invention. This prototype protection circuit 20 is particularly suitable for use in implantable cardiac therapy devices such as ICDs and pacemakers. However, it should be clearly understood that the utility of the present invention is not limited to these applications, but rather, may find use in any implantable medical device whose internal circuitry must be protected from current overload conditions.

In typical pacing, plethesmography (in which the impedance of a patient's heart is determined), and output capacitor discharge operations, an ICD is especially vulnerable to external high voltage transients. More particularly, at least two input/output (I/O) nodes are in a low impedance state during such operations, whereby external high voltage transients can induce large, potentially damaging currents through the host device. With this background in mind, the overload detection and protection circuit 20 was developed and is designed to drive an associated I/O node (there being one protection circuit for each I/O node to be protected) from a low-impedance state to a high-impedance state, to thereby place the host device in an overload protection mode which minimizes potential damage.

As will be developed in greater detail below, the protection circuit 20 is preferably designed to selectively place the host device in an overload protection mode only during those operations (or time periods) in which the host device is particularly vulnerable to external high voltage transients (e.g., during pacing and output capacitor discharge operations). Further, the protection circuit 20 is preferably designed to be automatically reset in order to return the associated I/O node to its normal low-impedance state after a prescribed overload protection mode time period has elapsed. Of course, many variations and/or modifications of these basic inventive concepts will become readily apparent to those having ordinary skill in the pertinent art without departing from the spirit and scope of the present invention, in its broadest sense.

With continuing reference to FIG. 1, the protection circuit 20 includes I/O terminal J1, NMOS transistors Q1, Q2, and Q3, resistors R1 and R2, a low-pass filter 22 comprised of a resistor R3 and a capacitor C1, a first inverter 23, a two-input NOR gate 25, a second inverter 27, a latch 29, and a reset switch 31. The NMOS transistor Q1 is connected between the I/O terminal J1 and a node A. The NMOS transistor Q2 is connected between the node A and ground through the resistor R1. The NMOS transistor Q3 is connected between ground and Vcc through the resistor R2. Node B intermediate the resistor R2 and the drain electrode of NMOS transistor Q3 is coupled to the input of the first inverter 23 through the low-pass filter 22. The output "OVLD" of the first inverter 23 is coupled to a first input of the NOR gate 25. A first control signal "CS1" is coupled to the second input of the NOR gate 25. The output of the NOR gate 25 is coupled to the input of the second inverter 27, whose output is coupled to a data input of the latch 29. The reset switch 31 has an input coupled to a second control signal "CS2" (or to the "OVLD" signal), and an output coupled to a control input of the latch 29. Outputs L1 and L2 of the latch 29 are coupled to the gates of the NMOS transistors Q1 and Q2, respectively.

In operation, the current overload detection and protection circuit 20 of the present invention works as follows. More particularly, a high voltage transient which appears at the I/O terminal J1 induces a large current through Q1, Q2, and R1, which constitutes a low-impedance path to ground, since the transistors Q1 and Q2 are normally turned on. As the induced current increases, the potential of node A increases. When the current reaches a prescribed threshold (e.g., >150 mA), the current through R1 will become large enough to bring the potential of node A higher than the threshold voltage (e.g., 0.7 V) of Q3, thereby turning transistor Q3 on. When Q3 turns on, current flows through R2, which pulls down the potential of node B to close to ground. If the potential at node B remains low for a time period greater than the time constant of the low-pass filter 22 (e.g., 1–10 ns), then the output "OVLD" of the first inverter 23 will go high. Thus, the signal "OVLD" constitutes a current overload detection signal whose logic level indicates whether a current overload condition has been detected. It will be appreciated that the low-pass filter 22 ensures that only high voltage transients that are sufficient to induce a large enough current (e.g., >150 mA) for greater than a prescribed time period (e.g., 1–10 ns) will result in detection of a current overload condition ("OVLD" being driven to a logic high level) by the protection circuit 20. In this way, the possibility of false detection of spurious signals which do not constitute potentially harmful high voltage transients is minimized. Of course, the specific thresholds and circuit parameters can be easily modified depending upon the requirements of the particular application.

Although not essential to the operation of the present invention, the "OVLD" signal is preferably supplied to the host device microprocessor (not shown) or other logic hardware which can be suitably programmed to change one or more prescribed operating parameters of the host device in response to a logic high level of the "OVLD" signal. In this connection, the "OVLD" signal can be classified as an interrupt signal and the host device microprocessor can be programmed to execute an "OVLD" interrupt handling routine in response to receipt of the "OVLD" interrupt signal from the protection circuit 20. For example, if the host device is an ICD which is currently in an operating mode in which it is delivering pacing, cardioversion, or defibrillation therapy (or other operating mode in which the device is particularly vulnerable to external high voltage transients), that operating mode could be disabled, inhibited, suspended, or delayed for a prescribed time period, e.g., for a fixed time period or for as long as the "OVLD" signal is at a logic high level. The temporary holding mode can be thought of as a "current overload protection mode of operation". Of course, many other responses (or non-responses) to the detection of a current overload condition can be envisioned by those skilled in the pertinent art without departing from the spirit and scope of the present invention, in its broadest sense.

Continuing now with the description of the protection circuit 20, the first control signal "CS1" which is coupled to the second of the NOR gate 25 is preferably at a logic low level at all times during normal operation of the host device, thereby effectively "enabling" the NOR gate 25, i.e., so that the output of the NOR gate 25 will transition from a logic high to a logic low level only in response to the "OVLD" signal transitioning from a logic low to a logic high level.

The output of the inverter 27 is of course the logical inverse of the output of the NOR gate 25, so that when the NOR gate 25 is "enabled" by the control signal "CS1", the output of the inverter 27 is at the same logic level as the "OVLD" signal. The outputs L1 and L2 of the latch 29 are the logical inverse of the output of the inverter 27, and thus, are at a logic level which is the inverse of the logic level of the "OVLD" signal. Thus, when a current overload condition is detected, the outputs L1 and L2 of the latch 29 turn off the transistors Q1 and Q2, respectively, to thereby switch the I/O terminal J1 from a low-impedance state to a high-impedance state, thereby deminimizing the potential of damage to the host device circuitry due to the presence of the external high voltage transient which induced the current overload condition in the first place. This state of the protection circuit 20 can be thought of as a "current overload protection mode" of the protection circuit 20.

The protection circuit 20 can alternatively be designed without the NOR gate 25 and the inverter 27, so that the "OVLD" signal can be applied directly to the latch 29, (or with the second input of the NOR gate 25 connected to ground rather than to the first control signal "CS1"). In fact, although the latch 29 (e.g., a bistable latch) is highly recommended in order to ensure stable and reliable operation of the protection circuit 30, the latch 29 can also be dispensed with (in which case the inverter 27 is re-inserted), whereby the output of the inverter 27 can be applied directly to the gates of the transistors Q1 and Q2, to thereby turn off the transistors Q1 and Q2 when a current overload condition is detected, to thereby switch the I/O terminal J1 from a low-impedance state to a high-impedance state, thereby minimizing the potential of damage to the host device circuitry due to the presence of the external high voltage transient which induced the current overload condition in the first place.

Alternatively, a NAND gate can be used in place of the NOR gate 25, with the first control signal "CS1" being at a logic low level only at such times that the host device is in a particularly vulnerable mode of operation. In this case, the protection circuit 20 is operable only at times when the host device is in a particularly vulnerable mode of operation and a high voltage transient is detected to drive the I/O terminal J1 from a low-impedance state to a high-impedance state (i.e., both inputs to the NAND gate must be logic high in order to drive the output of the inverter 27 to a logic high level).

In an implementation of the protection circuit 20 in which a latch, such as the latch 29, is utilized, it is preferable that an automatic reset mechanism such as the reset switch 31 be employed in order to automatically reset the latch 29 a prescribed time (e.g., 1 second) after the current overload condition is detected, thereby driving the outputs L1 and L2 of the latch 29 to a logic high level, whereby the transistors Q1 and Q2, respectively, will be turned on, thereby returning the I/O terminal J1 to its normal low-impedance state. In this connection, the reset switch 31 can have a built-in timer or other delay circuitry, so that its output is driven to a logic high level a fixed time after the "OVLD" signal goes high. Alternatively, the reset switch 31 can be responsive to a second control signal "CS2" generated by the host device microprocessor (or other logic hardware) to generate the reset signal for resetting the latch 29. In this case, the time delay between the time when the "OVLD" signal goes high and the time the reset signal is generated can be varied, e.g., depending upon the current operating mode of the host device. Another alternative is that the reset switch 31 be implemented as a Schmitt trigger, monostable multivibrator, or other one-shot device which is triggered on the trailing edge of the "OVLD" signal, so that the latch 29 is automatically reset in response to the current overload condition no longer being detected (i.e., when "OVLD" goes from a high logic level to a low logic level). Thus, the latch 29 can be reset and the I/O terminal J1 driven to its normal low-impedance state coincident with the cessation of the current overload condition.

In general, although an exemplary prototype implementation of the present invention has been described in detail hereinabove, it should be clearly understood that many other variations and/or modifications of the basic inventive concepts taught herein which may appear to those skilled in the pertinent art will still fall within the spirit and scope of the present invention, as defined in the appended claims. For example, inverse logic could be employed and/or various circuit elements could be omitted or modified and/or various circuit elements could be added, without departing from the spirit and scope of the present invention.

What is claimed is:

1. A circuit for protecting a host device from potential damage due to high voltage transients applied to an I/O node thereof, comprising:
    an I/O circuit coupled to the I/O node, the I/O circuit having low-impedance and high-impedance modes;
    a current overload detection circuit coupled to the I/O circuit which detects a current overload condition induced by a high voltage transient applied to the I/O node, and which generates an overload detect signal in response to detecting a current overload condition;
    a mode changing circuit which changes the mode of the I/O circuit from the low-impedance mode to the high-impedance mode in response to the overload detect signal; and
    a reset circuit which generates a reset signal a prescribed time after the overload detect signal is generated, wherein the mode changing circuit is responsive to the reset signal to change the mode of the I/O circuit from the high-impedance mode to the low-impedance mode.

2. The circuit as set forth in claim 1, wherein the host device is an implantable cardiac therapy device.

3. A circuit for protecting a host device from potential damage due to high voltage transients applied to an I/O node thereof, comprising:
    an I/O circuit cooled to the I/O node, the I/O circuit having low-impedance and high-impedance modes and comprising:
        a first MOS transistor having a first electrode coupled to the I/O node, a second electrode coupled to a first node, and a gate electrode;
        a second MOS transistor having a first electrode coupled to the first node, a second electrode, and a gate electrode; and,
        a first resistor having a first end coupled to the second electrode of the second MOS transistor and a second end coupled to a reference voltage;
    a current overload detection circuit coupled to the I/O circuit which detects a current overload condition induced by a high voltage transient applied to the I/O node, and which generates an overload detect signal in response to detecting a current overload condition; and,
    a mode changing circuit which changes the mode of the I/O circuit from the low-impedance mode to the high-impedance mode in response to the overload detect signal.

4. The circuit as set forth in claim 3, wherein the current overload detection circuit comprises:
    a third MOS transistor having a first electrode coupled to the reference voltage, a second electrode, and a gate electrode coupled to the first node;
    a second resistor having a first end coupled to the second electrode of the third MOS transistor, and a second end coupled to a power supply voltage; and,
    wherein the potential of a second node intermediate the second electrode of the third MOS transistor and the first end of the second resistor is indicative of the presence of a current overload condition.

5. The circuit as set forth in claim 4, wherein the current overload detection circuit further comprises:

a first inverter having an input and an output;

a low-pass filter coupled between the second node and the input of the first inverter; and, wherein the output of the first inverter comprises the overload detect signal.

6. The circuit as set forth in claim 5, wherein the mode changing circuit comprises:

a logic gate having a first input coupled to the overload detect signal and a second input coupled to a control signal, and an output;

a mode control circuit coupled to the output of the logic gate; and, wherein the first and second MOS transistors are turned off in response to a prescribed logic level of the output of the logic gate, to thereby place the circuit in a current overload protection mode of operation.

7. The circuit as set forth in claim 6, wherein the mode control circuit includes:

an inverter having an input coupled to the output of the logic gate, and an output;

a latch having an input coupled to the output of the inverter and a first output coupled to the gate electrode of the first MOS transistor and a second output coupled to the gate electrode of the second MOS transistor; and, wherein the first and second MOS transistors are turned off in response to the first and second outputs of the latch in the current overload protection mode of operation.

8. The circuit as set forth in claim 3, wherein the current overload detection circuit includes first sense circuitry which ensures that the overload detect signal is generated only when an overload current flowing through the I/O circuit is greater than a prescribed threshold level.

9. The circuit as set forth in claim 8, wherein the current overload detection circuit further includes second sense circuitry which ensures that the overload detect signal is generated only when the overload current exceeds the prescribed threshold level for at least a prescribed time period.

10. The circuit as set forth in claim 9, further comprising a reset circuit which generates a reset signal a prescribed time after the overload detect signal is generated, wherein the mode changing circuit is responsive to the reset signal to change the mode of the I/O circuit from the high-impedance mode to the low-impedance mode.

11. A circuit for protecting a host device from potential damage due to high voltage transients applied to an I/O node thereof, comprising:

an I/O circuit coupled to the I/O node, the I/O circuit having low-impedance and high-impedance modes;

a current overload detection circuit coupled to the I/O circuit which detects a current overload condition induced by a high voltage transient applied to the I/O node, and which generates an overload detect signal in response to detecting a current overload condition; and, a mode changing circuit which changes the mode of the I/O circuit from the low-impedance mode to the high-impedance mode in response to the overload detect signal, the mode changing circuit including logic circuitry which generates a mode change control signal only when both the overload detect signal and a first control signal are present and mode changing circuitry which changes the mode of the I/O circuit from the low-impedance mode to the high-impedance mode in response to the mode change control signal.

12. The circuit as set forth in claim 11, wherein the first control signal is present only when the host device is in a prescribed operating mode in which it is particularly vulnerable to damage due to the high voltage transients.

13. The circuit as set forth in claim 12, further comprising a reset circuit which generates a reset signal a prescribed time after the first control signal is generated, wherein the mode changing circuit is responsive to the reset signal to change the mode of the I/O circuit from the high-impedance mode to the low-impedance mode.

14. The circuit as set forth in claim 13, wherein the reset circuit generates the reset signal in response to a second control signal.

15. The circuit as set forth in claim 14, wherein the first and second control signals are generated by a host device microprocessor.

16. A circuit for protecting a host device from potential damage due to high voltage transients applied to an I/O node thereof, comprising:

an I/O circuit coupled to the I/O node, the I/O circuit having low-impedance and high-impedance modes;

current overload detection means coupled to the I/O circuit for detecting a current overload condition induced by a high voltage transient applied to the I/O node, and for generating an overload detect signal in response to detecting a current overload condition;

mode changing means for changing the mode of the I/O circuit from the low-impedance mode to the high-impedance mode in response to the overload detect signal; and, reset means for generating a reset signal a prescribed time after the overload detect signal is generated, wherein the mode changing means is responsive to the reset signal to change the mode of the I/O circuit from the high-impedance mode to the low-impedance mode.

17. The circuit as set forth in claim 16, wherein the current overload detection means includes first means for ensuring that the overload detect signal is generated only when an overload current flowing through the I/O circuit is greater than a prescribed threshold level the current overload detection circuit, and second means for ensuring that the overload detect signal is generated only when the overload current exceeds the prescribed threshold level for at least a prescribed time period.

18. The circuit as set forth in claim 16, wherein the host device is an implantable cardiac therapy device.

* * * * *

UNITED STATES PATENT AND TRADEMARK OFFICE
CERTIFICATE OF CORRECTION

PATENT NO.    : 5,968,083

DATED         : October 19, 1999

INVENTOR(S)   : Ciciarelli, et. al.

It is certified that error appears on the above-identified patent and that said Letters Patent is hereby corrected as shown below:

Col. 1, Line 42, "tenninate" should be "terminate"

Col. 6, Claim 3, Line 36 "cooled" should be "coupled"

Signed and Sealed this

Twenty-fourth Day of October, 2000

Attest:

Q. TODD DICKINSON

Attesting Officer        Director of Patents and Trademarks